United States Patent
Kim et al.

(10) Patent No.: US 11,433,110 B2
(45) Date of Patent: Sep. 6, 2022

(54) **COMPOSITION FOR TREATING FINE DUST-CAUSED SKIN CELL DAMAGE OR FOR INHIBITING ANTIMICROBIAL PEPTIDE, COMPRISING *HIBISCUS SYRIACUS* EXTRACT**

(71) Applicant: AMOREPACIFIC CORPORATION, Seoul (KR)

(72) Inventors: Hyoung-June Kim, Yongin-si (KR); Tae Ryong Lee, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

(21) Appl. No.: 16/651,880

(22) PCT Filed: Aug. 20, 2018

(86) PCT No.: PCT/KR2018/009516
§ 371 (c)(1),
(2) Date: Mar. 27, 2020

(87) PCT Pub. No.: WO2019/066252
PCT Pub. Date: Apr. 4, 2019

(65) Prior Publication Data
US 2020/0230186 A1 Jul. 23, 2020

(30) Foreign Application Priority Data
Sep. 29, 2017 (KR) .................. 10-2017-0127665
Sep. 29, 2017 (KR) .................. 10-2017-0127667

(51) Int. Cl.
| | |
|---|---|
| A61K 36/00 | (2006.01) |
| A61K 36/185 | (2006.01) |
| A23L 33/105 | (2016.01) |
| A61K 8/9789 | (2017.01) |
| A61Q 19/00 | (2006.01) |

(52) U.S. Cl.
CPC .......... *A61K 36/185* (2013.01); *A23L 33/105* (2016.08); *A61K 8/9789* (2017.08); *A61Q 19/00* (2013.01); *A23V 2002/00* (2013.01)

(58) Field of Classification Search
None
See application file for complete search history.

(56) References Cited

U.S. PATENT DOCUMENTS

2014/0106009 A1   4/2014   Matheson

FOREIGN PATENT DOCUMENTS

| JP | 04-077432 | * | 3/1992 |
|---|---|---|---|
| JP | 2003-171300 | A | 6/2003 |
| JP | 2007-119432 | A | 5/2007 |
| KR | 10-2010-0059302 | | 6/2010 |
| KR | 10-2010-0080164 | A | 7/2010 |
| KR | 10-0985719 | B1 | 10/2010 |
| KR | 10-1065718 | B1 | 9/2011 |
| KR | 10-2014-0033039 | A | 3/2014 |
| KR | 10-1490762 | B1 | 2/2015 |
| KR | 10-1629706 | B1 | 6/2016 |
| KR | 10-2017-0024267 | A | 3/2017 |
| WO | 2012/138906 | A2 | 10/2012 |
| WO | 2017/043868 | A1 | 3/2017 |

OTHER PUBLICATIONS

Ah Ram Jang, "A Study on Cosmetic Physiological and Skin Cell Activity of Hibiscus syriacus Extracts", Master's Thesis, Dept, of Graduate School of Social Culture, Hannam University, 2012, pp. 8-29.
Eui Dong Son, et al., "S100A7 (psoriasin) inhibits human epidermal differentiation by enhanced IL-6 secretion through IkB/NF-kB signalling", Experimental Dermatology, 2016, vol. 25, pp. 636-641.
Hyoung-June Kim, et al., "Transcriptome analysis of airborne PM2.5-induced detrimental effects on human keratinocytes", Toxicoloy Letters, 2017, vol. 273, pp. 26-35.
International Search Report for PCT/KR2018/009516 dated Mar. 5, 2019 (PCT/ISA/210).
Chinese Patent Office, Communication dated Jul. 8, 2022 in copending Chinese Application No. 201880077667.8.

* cited by examiner

*Primary Examiner* — Michael V Meller
(74) *Attorney, Agent, or Firm* — Sughrue Mion, PLLC (57) ABSTRACT

Disclosed is a composition including a *Hibiscus syriacus* extract as an effective ingredient for treating fine dust-caused skin damage, wherein the expression of at least one selected from the group consisting of IL-36G (NM_019618), PTGS2 (NM_000963), XDH (NM_000379) and S100A7 (NM_002963), which are all genes having the expression levels affected by fine dust in skin cells, is regulated to a normal level and for inhibiting an antibacterial peptide, wherein the expression of the antibacterial peptide S100A7 (NM_002963) is regulated to a normal level. By using the composition for treating fine dust-caused skin damage and the composition for inhibiting an antibacterial peptide, gene expression changed by fine dust can return to a normal level to treat skin cell damage and the increased expression of the antibacterial peptide due to various causes can return to normal level.

8 Claims, 5 Drawing Sheets

COMPOSITION FOR TREATING FINE DUST-CAUSED SKIN CELL DAMAGE OR FOR INHIBITING ANTIMICROBIAL PEPTIDE, COMPRISING *HIBISCUS SYRIACUS* EXTRACT

CROSS-REFERENCE TO RELATED APPLICATION

This application is a National Phase of International Application No. PCT/KR2018/009516, filed on Aug. 20, 2018, which claims priority to Korean Patent Application Nos. 10-2017-0127665 and 10-2017-0127667, both filed on Sep. 29, 2017, and all the benefits accruing therefrom under 35 U.S.C. § 119, the contents of which in its entirety are herein incorporated by reference.

TECHNICAL FIELD

Disclosed in the present disclosure is a composition for treating skin cell damage caused by fine dust or inhibiting an antimicrobial peptide. More specifically, disclosed is a composition comprising a *Hibiscus syriacus* extract, which treats skin cell damage by significantly changing the expression level of biomarkers, etc., which are skin cell genes the expression level of which is changed by fine dust as compared to skin cells in normal state, or significantly changes the expression level of an antimicrobial peptide changed as compared to skin cells in normal state due to various causes.

BACKGROUND ART

Skin is a part of the body that is directly exposed to the external environment. It not only serves as a protective layer for protecting important organs of our body, but also regulates water evaporation and protects the body from external infections. However, even though the skin prevents viral invasion from the outside, excessive exposure of the skin to ultraviolet rays or pollutants causes skin irritation. Particularly, the skin is damaged by Asian dust which is accompanied by strong wind and dirt.

Asian dust is a phenomenon in which small-sized sands or red clays float from the inland deserts of China, Mongolia, etc., are carried far away by the upper winds and then drop near the ground. In Korea, Asian dust occurs periodically every spring. Asian dust is a combination of organic and inorganic materials, and its physical characteristics and constituents are very diverse depending on the time and place of occurrence. It also includes metals that can have biological effects. The larger-sized particles of Asian dust usually stay in or around their, and the smaller-sized particles thereof flow even into Korea. It is reported that, when inhaled, this dust is deposited in the lower bronchial tubes and even in the gas exchange part of the lungs, which may cause damage to the respiratory system. In addition, it was found that skin cell damage was increased in the skin of people living in areas with lots of Asian dust or dirt.

Antimicrobial peptides, which are substances similar to antibiotics in their functions and known to be effective in enhancing immunity, are drawing a lot of attentions recently. The antimicrobial peptides are a part of the nonspecific immune defense system of microorganisms, plants, insects, amphibians and mammals against microbial invasion from outside. The antimicrobial peptide contains a number of positively charged amino acids in its sequence structurally, and exhibits broad-spectrum antibiotic activity against Gram-positive bacteria, Gram-negative bacteria, fungi and cancerous cells.

When bound to cell membranes, these peptides inhibit energy production by microorganisms by forming ion channels or large pores in the cell membranes, thereby killing cells. As such, they have the mechanism of action of destroying cell membranes physically in short time nonspecifically and effectively.

However, excessive antimicrobial peptides may have harmful effects on the contrary. For example, S100A7, which is a member of the S100 protein family, is a well-known antimicrobial peptide. Although the accurate mechanisms are not known, it is known that the treatment with the recombinant S100A7 peptide impairs epidermal differentiation, and that the antimicrobial protein S100A7 acts as a negative regulator in epidermal differentiation when present in excess in skin cells with atopic dermatitis (AD) and psoriatic lesions (see non-patent document 1).

Accordingly, as a measure of treating skin cell damage, it is necessary to inhibit antimicrobial peptides in skin cells.

REFERENCES OF RELATED ART

Non-Patent Documents (Non-patent document 1) Son et al., "S100A7 (psoriasin) inhibits human epidermal differentiation by enhanced IL-6 secretionh through IκB/NF-κB signalling", *Experimental Dermatology*. 2016 August; 25(8): 636-41.

(Non-patent document 2) Kim, H. J., et al, "Transcriptome analysis of airborne $PM_{2.5}$-induced detrimental effects on human keratinocytes", *Toxicology Letters* 273, 26-35, 2017.

DETAILED DESCRIPTION OF THE INVENTION

Technical Problem

In an aspect, the present disclosure is directed to providing composition for inhibiting an antimicrobial peptide.

The present inventors have found that fine dust has harmful effects on skin, which affect the expression of skin cell genes, thereby causing symptoms such as damages of skin cells, etc.

Accordingly, in an aspect, the present disclosure is directed to providing a composition for treating skin cell damage caused by fine dust.

Technical Solution

In an aspect, the present disclosure provides, as a composition comprising a *Hibiscus syriacus* extract as an active ingredient, a composition for treating skin damage caused by fine dust, which regulates the expression level of one or more selected from a group consisting of IL-36G (NM_019618), PTGS2 (NM_000963), XDH (NM_000379) and S100A7 (NM_002963), which are genes in skin cells the expression level of which is affected by fine dust, to a normal level.

In another aspect, the present disclosure provides, as a composition comprising a *Hibiscus syriacus* extract as an active ingredient, a composition for inhibiting an antimicrobial peptide, which regulates the expression level of the antimicrobial peptide S100A7 (NM_002963) to a normal level.

Advantageous Effects

In an aspect, by using a composition for treating skin damage caused by fine dust, skin cell damage can be treated by returning the expression level of the genes changed by fine dust to a normal level.

In another aspect, by using a composition for inhibiting an antimicrobial peptide, the expression level of the antimicrobial peptide increased due to various causes can be returned to a normal level.

DETAILED DESCRIPTION OF THE PREFERRED EMBODIMENTS

Hereinafter, the present disclosure is described in detail.

In an aspect of the present disclosure, a composition for treating skin damage caused by fine dust may comprise a *Hibiscus syriacus* extract as an active ingredient.

In an aspect of the present disclosure, a composition for inhibiting an antimicrobial peptide may comprise a *Hibiscus syriacus* extract as an active ingredient.

*Hibiscus syriacus* is a deciduous dicotyledonous shrub in the family Malvaceae of the order Malvales. The plant is 3-4 m in height. Young branches have furs, which disappear gradually. *Hibiscus syriacus* can be easily grown in gardens. Although *Hibiscus syriacus* can be propagated from seeds, it is easy to maintain its genetic characteristics without change since it can also be propagated by cutting. The leaves are alternate, ovate, usually divided into three parts, and have toothed margins. The external skin of *Hibiscus syriacus* may be peeled off for use as a raw material of paper or medicine. Young leaves can be eaten, and the flowers and leaves can be brewed into tea.

The main ingredient of the flower of *Hibiscus syriacus* is saponarin, which is an antioxidant effective in relieving phlegm. It is known that tannic acid is contained in the root and bark of *Hibiscus syriacus*, saponarin in the flowers and leaves, and malvalic acid, sterculic acid, etc. in the seeds.

According to Dongui Bogam and Pen-tsao Kang-mu, the root and bark are decocted or brewed and applied or fomented to treat athlete's foot, hemorrhoids or pain, the flower and leaf are dried, powdered and taken together with warm water to relieve phlegm, quench thirst, treat vomiting, recover appetite, etc., and the seeds are scorched and smoked to treat headache, migraine or abscess. In addition, *Hibiscus syriacus* is effective in hemorrhage, fever, detoxification, female disorder, scabies, pain, spasm, hair growth, hair loss, bronchial trouble, sore throat, enteritis, dysentery, hernia, etc.

In the past, the steamed leaf of *Hibiscus syriacus* was used in Korea as food during periods of famine. The petal of *Hibiscus syriacus* was used to prepare rice cake and tea, young leaf of *Hibiscus syriacus* for potherbs and beanpaste potage, and root for wine. In Europe and China, the leaf and flower were used for herbal tea, and flower bud was used as a flavor in royal court cuisine. In addition, the fiber obtained from the bark of *Hibiscus syriacus* is used for papermaking.

In an aspect, the leaf, stem, bark, root, fruit, bud, seed, etc. of *Hibiscus syriacus* may be used in the composition of the present disclosure. Specifically, an extract of the leaf, stem, bark, root, fruit, bud, seed, etc. of *Hibiscus syriacus* may be used in the composition of the present disclosure. In an exemplary embodiment, the bark extract of *Hibiscus syriacus* may be used in the composition of the present disclosure.

In an aspect of the present disclosure, the *Hibiscus syriacus* extract may be prepared by extracting *Hibiscus syriacus* with an extraction solvent.

In an aspect of the present disclosure, the *Hibiscus syriacus* extract may be prepared by extracting *Hibiscus syriacus* with water or an organic solvent. Specifically, it may be prepared by extracting *Hibiscus syriacus* with one or more extraction solvent selected from a group consisting of water, a $C_1$-$C_6$ anhydrous or water-containing lower alcohol, acetone, butylene glycol, ethyl acetate, diethyl acetate, diethyl ether, benzene, chloroform and hexane.

In an aspect, the *Hibiscus syriacus* extract may be extracted at room temperature.

In an aspect, the *Hibiscus syriacus* extract may be obtained by extracting with the extraction solvent and then further performing one or more of evaporation, filtration, concentration, separation and drying. In particular, the *Hibiscus syriacus* extract may be subjected to one or more filtration process. In an exemplary embodiment, it is subjected to two filtration processes.

In an exemplary embodiment, the separation process may include a centrifugation process.

Specifically, the extraction may be performed using one or more of a polar solvent including water, a $C_1$-$C_6$ anhydrous or water-containing lower alcohol, acetone and butylene glycol and a low-polarity solvent including ethyl acetate, diethyl acetate, diethyl ether, benzene, chloroform and hexane as a solvent.

More specifically, the solvent may be a 50-90% ethanol aqueous solution and may be a 60-80% or 65-75% ethanol aqueous solution. When the solvent is a 50-90% ethanol aqueous solution, the active ingredient can be effectively extracted from *Hibiscus syriacus*. In one embodiment, the solvent may be an about 70% ethanol aqueous solution.

In an aspect, the extract may be concentrated under reduced pressure at an appropriate temperature in a distillation apparatus equipped with a cooling condenser after the extraction.

However, the *Hibiscus syriacus* extract according to the present disclosure can be obtained by extraction according to a common method in the art, and the extraction method is not limited to the above-described methods.

In an aspect of the present disclosure, the composition may contain 0.000001-30 wt % of the *Hibiscus syriacus* extract based on the total weight of the composition. When the content thereof is 0.000001-30 wt %, the *Hibiscus syriacus* extract exhibits an excellent effect of treating skin damage caused by fine dust.

Specifically, the content may be 0.0000001 wt % or more, 0.0000005 wt % or more, 0.0000007 wt % or more, 0.0000009 wt % or more, 0.000001 wt % or more, 0.000002 wt % or more, 0.000004 wt % or more, 0.000006 wt % or more, 0.000008 wt % or more, 0.00001 wt % or more, 0.00003 wt % or more, 0.00005 wt % or more, 0.00007 wt % or more, 0.00009 wt % or more, 0.0001 wt % or more, 0.0003 wt % or more, 0.0005 wt % or more, 0.0007 wt % or more, 0.0009 wt % or more, 0.001 wt % or more, 0.01 wt % or more, 0.1 wt % or more, 1 wt % or more, 3 wt % or more, 5 wt % or more, 7 wt % or more, 9 wt % or more, 10 wt % or more, 13 wt % or more, 15 wt % or more, 17 wt % or more, 19 wt % or more, 21 wt % or more, 23 wt % or more, 25 wt % or more, 27 wt % or more, 29 wt % or more, 30 wt % or more or 31 wt % or more, and 32 wt % or less, 31 wt % or less, 30 wt % or less, 29 wt % or less, 28 wt % or less, 26 wt % or less, 24 wt % or less, 22 wt % or less, 20 wt % or less, 18 wt % or less, 16 wt % or less, 14 wt % or less, 12 wt % or less, 10 wt % or less, 9 wt % or less, 8 wt % or less, 6 wt % or less, 4 wt % or less, 2 wt % or less, 1 wt % or less, 0.1 wt % or less, 0.09 wt % or less, 0.04 wt % or less, 0.01 wt % or less, 0.006 wt % or less, 0.001 wt % or less, 0.0009 wt % or less, 0.0007 wt % or less, 0.00005 wt % or less, 0.00003 wt % or less, 0.00001 wt % or less, 0.000009 wt % or less, 0.000007 wt % or less, 0.000005 wt % or less, 0.000003 wt % or less, 0.000001 wt % or less, 0.0000009 wt % or less, 0.0000007 wt % or less, 0.0000005 wt % or less, 0.0000003 wt % or less, 0.0000002 wt % or less, 0.0000001 wt % or less or 0.00000009 wt % or less, although not being limited thereto.

In another aspect, the present disclosure, the composition is for treating skin damage caused by fine dust.

The term "fine dust" used in the present disclosure refers to very small particulate matter invisible to human eyes, which floats or flutters in the atmosphere for a long time. It may refer to dust with a particle diameter of 10 μm or less. In particular, the particulate matter having a particle diameter of 2.5 μm or less is called "ultrafine dust". In the present disclosure, the term "fine dust" is intended to include "ultrafine dust".

In the present disclosure, the term "treatment" refers to effective protection of skin cells from irritation and inhibition, prevention or restoration (recovery) of change in the expression level of a specific gene by the irritation.

In another aspect, the present disclosure provides a method for treating skin damage of a subject caused by fine dust, comprising administering a composition comprising a *Hibiscus syriacus* extract as an active ingredient to a subject in need thereof.

In another aspect, the present disclosure provides a use of a *Hibiscus syriacus* extract in the manufacture of a composition for treating skin damage caused by fine dust.

In another aspect, the present disclosure provides a *Hibiscus syriacus* extract for treating skin damage caused by fine dust.

In an aspect, the present disclosure provides a composition for inhibiting skin damage caused by fine dust by regulating the expression level of specific genes in skin cells damaged by fine dust to a normal level.

Specifically, in the present disclosure, the genes in skin cells the expression level of which is affected by fine dust may include IL-36G (NM_019618), PTGS2 (NM_000963), XDH (NM_000379), S100A7 (NM_002963), etc. Since the IL-36G (NM_019618), PTGS2 (NM_000963), XDH (NM_000379) and S100A7 (NM_002963) are the genes the expression level of which is increased by fine dust, skin cell damage can be inhibited by reducing the expression level of these genes to a normal level.

The genes used in the present disclosure, the expression level of which is increased by fine dust, are listed in Table 1. Table 1 shows the genes the expression level of which is increased by fine dust. In the table, the "name" is the GeneBank accession ID of the NCBI, the "gene symbol" is the official gene symbol, and the "gene title" is the name of each gene. They are described in the non-patent document 1.

TABLE 1

| | Increased genes | |
|---|---|---|
| Name | Gene symbol | Gene title |
| NM_019618 | IL36G | Interleukin 36, gamma |
| NM_000963 | PTGS2 | Cyclooxygenase-2 (COX-2) |
| NM_000379 | XDH | Xanthine dehydrogenase |
| NM_002963 | S100A7 | S100 calcium-binding protein A7 |

In another aspect, the present disclosure provides a use of the composition for inhibiting an antimicrobial peptide.

In another aspect, the present disclosure provides a method for inhibiting an antimicrobial peptide in a subject. The method may comprise administering a composition comprising a *Hibiscus syriacus* extract as an active ingredient to a subject in need thereof.

In another aspect, the present disclosure provides a use of a *Hibiscus syriacus* extract in the manufacture of a composition for inhibiting an antimicrobial peptide.

In another aspect, the present disclosure provides a *Hibiscus syriacus* extract for inhibiting an antimicrobial peptide.

In an aspect, the present disclosure provides a composition for inhibiting an antimicrobial peptide by regulating the expression level of specific genes in skin cells to a normal level.

Specifically, the expression level of the antimicrobial peptide S100A7 (NM_002963) may be affected by various causes. When the expression level of the antimicrobial peptide S100A7 (NM_002963) is increased due to such causes, the antimicrobial peptide may be inhibited by regulating the expression level of the gene to a normal level by using the composition.

The gene used in the present disclosure, the expression level of which is increased by various causes, is described in Table 2. Table 2 shows the antimicrobial peptide gene the expression level of which is increased. In the table, the "name" is the GeneBank accession ID of the NCBI, the "gene symbol" is the official gene symbol, and the "gene title" is the name of the gene. It is described in the non-patent document 2.

TABLE 2

| | Increased genes | |
|---|---|---|
| Name | Gene symbol | Gene title |
| NM_002963 | S100A7 | S100 calcium-binding protein A7 |

The expression level of these genes or proteins may be analyzed using various analysis methods known in the art, such as microarray, PCR, NGS (next-generation sequencing), western blot, northern blot, ELISA, radioimmunoassay, radioimmunodiffusion, immunohistochemical staining, immunoprecipitation assay, etc.

In an aspect of the present disclosure, the composition may be a cosmetic composition, a pharmaceutical composition or a health functional food composition.

For example, the cosmetic composition may be a cosmetic such as a cream, a lotion, a toner, a cleanser, a face cleanser, a soap, a beauty care solution, etc.

In an aspect, the cosmetic to which the composition containing a *Hibiscus syriacus* extract of the present disclosure is added may be in the form of a solution, an emulsion, a viscous mixture, etc.

That is to say, in an aspect, the formulation of the cosmetic of the present disclosure is not particularly limited. For example, the formulation may be an emulsion, a cream, a toner, an essence, a pack, a gel, a powder, a makeup base, a foundation, a lotion, an ointment, a patch, a cosmetic solution, a cleansing foam, a cleansing cream, a cleansing water, a body lotion, a body cream, a body oil, a body essence, a shampoo, a rinse, a body cleanser, a soap, a hair dye, a spray, etc.

Ingredients other than the *Hibiscus syriacus* extract may be selected and added to the cosmetic composition of each formulation without difficulty by those skilled in the art in consideration of the formulation or purpose of use.

In addition, in an aspect, the cosmetic of the present disclosure may contain one selected from a group consisting of a water-soluble vitamin, an oil-soluble vitamin, a polypeptide, a polysaccharide, a sphingolipid and a seaweed extract.

In addition, in an aspect, the cosmetic of the present disclosure may contain ingredients that are generally used in cosmetics in addition to the essential ingredient, if necessary.

Examples of the additional ingredients include oils and fats, moisturizers, emollients, surfactants, organic and inorganic pigments, organic powders, UV absorbers, preservatives, sterilizers, antioxidants, plant extracts, pH adjusters, alcohols, colorants, fragrance, blood circulation stimulants, skin coolers, antiperspirants, purified water, etc.

However, the ingredients that may be contained in the cosmetic are not limited thereto. Also, the amount of any of the ingredients may be determined within a range not negatively affecting the purpose and effect of the present disclosure.

In an aspect, the pharmaceutical composition comprising a *Hibiscus syriacus* extract of the present disclosure may further comprise a suitable carrier, excipient and diluent commonly used for preparation of pharmaceutical compositions.

The pharmaceutical composition comprising a *Hibiscus syriacus* extract may be formulated into any form suitable for pharmaceutical preparations, including oral formulations such as a tablet, a capsule, a powder, a syrup, etc. and agents for external application to the skin such as an ointment, a gel, a cream, a patch, a spray, etc. according to common methods.

In general, it is to be understood that the actual dosage of the active ingredient administered by the pharmaceutical composition should be determined in light of various relevant factors such as the severity of the symptom, the selected administration route, the age, gender, body weight and health condition of a subject, etc. In general, the dosage of the active ingredient may be 0.0001-3000 mg/kg/day, for example, 10-500 mg/kg/day.

In the health functional food composition according to an aspect of the present disclosure, the health food may refer to a food prepared from nutrients which are likely to be deficient in normal diets or raw materials or ingredients (functional raw materials) with functions useful for the human body, and which maintain and improve health by maintaining the normal function of the human body or activating physiological functions, although not being limited thereto. The health food may be prepared and processed into the form of a tablet, a capsule, a powder, a granule, a liquid, a pill, etc. However, the formulation is not limited thereto, and it may be prepared and processed into any form under the law.

Specifically, a health beverage composition is not particularly limited in ingredients other than the above-described compound contained in the predetermined ratio as an essential ingredient. It may contain various flavoring agents or natural carbohydrates as additional ingredients as in common beverages. Examples of the natural carbohydrates are conventional sugars such as a monosaccharide, a polysaccharide, a cyclodextrin, etc. and sugar alcohols such as xylitol, sorbitol, erythritol, etc. Also, natural flavoring agents (thaumatin, *stevia* extract (e.g., rebaudioside A, glycyrrhizin, etc.)) and synthetic flavoring agents (e.g., saccharin, aspartame, etc.) may be used as the flavoring agent.

In general, it is to be understood that the actual dosage of the active ingredient administered by the health functional food composition should be determined in light of various relevant factors such as the severity of the symptom, the selected administration route, the age, gender, body weight and health condition of a subject, etc. In general, the dosage of the active ingredient may be 0.0001-1000 mg/kg/day, for example, 0.02-6 mg/kg/day.

Hereinafter, the constitution and effect of the present disclosure will be described in more detail with reference to examples. However, the following examples are provided for illustrative purposes only to facilitate understanding of the present disclosure, and the scope of the present disclosure is not limited thereto.

[Example 1] Preparation of *Hibiscus syriacus* Extract

*Hibiscus syriacus* cultivated in Gyeongsangbuk-do, Korea was purchased from Morechem. The bark of *Hibiscus syriacus* was extracted at room temperature using an extraction solvent obtained by mixing purified water and ethanol at a ratio of 3:7, i.e., 70% ethanol, as an extraction solvent, and then the alcohol was evaporated. After the extraction at room temperature, primary filtration was performed to remove the solid material contained in the extract. Then, the extract was concentrated to remove ethanol, followed by separation and purification. Then, the resultant was subjected to centrifugation and secondary filtration, and then dried to obtain a *Hibiscus syriacus* extract.

[Example 2] Collection and Extraction of Fine Dust

Fine dust was collected using a low-volume air sampler (Sensidyne, Gillian, Fla., USA). The filter and denuder of a filter pack were replaced around 10:00 am on each measurement day, and the sample was collected for about 24 hours. Fine dust was collected daily for 28 days in an area downwind from Seoul, Korea (on the rooftop of a six-story building (Hankuk University of Foreign Studies, Center for International Studies, Residence Hall), Cheoin-gu, Yongin-si, Gyeonggi-do). Sampling time was recorded by checking the time while a vacuum pump was operated using a timer. Sampling rate, which was set to 16.7 L/min, was measured when the sampling was started and finished using a flow meter (Model 4143, TSI Inc.). A Teflon filter loaded into the filter pack was weighed before and after the sampling. Before weighing the Teflon filter, it was settled for 24 hours in a desiccator (Nikko, Japan) of 40% relative humidity. The weight was measured twice using an electronic balance (DVG215CD, Ohaus) to the five digits to the right of the decimal point and then averaged. Also, after the sampling, the filter was weighed twice after settlement in a desiccator for 24 hours. Mass concentration was calculated from the weight measured before the sampling. The fine dust was extracted as follows. The Teflon filter was soaked in 1 mL of ethanol. After adding 14 mL of DW so that the water level reached the aerosol sampling surface of the filter, followed by capping, extraction was conducted for 30 minutes by sonication. After completely removing water from the filter in a desiccator for 48 hours to minimize error, the weight of the filter before and after the extraction was measured using a high-precision balance (Mettler Toledo Company) which can measure up to 0.1 mg.

[Example 3] Culturing of (Normal Human) Keratinocytes

Keratinocytes (normal human epidermal keratinocytes) purchased from Lonza, Inc. (Walkersville, Md., USA) were subcultured and then cultured in a $CO_2$ incubator under the condition of 37° C. and 5% $CO_2$. The cells were cultured according to Lonza's guidelines. The KGM-2 Bullet kit CC-3107 in which the KGM-2 Bullet kit CC-4152 (BPE (bovine pituitary extract), human epidermal growth factor (hEGF), insulin, hydrocortisone, transferrin, epinephrine and gentamycin sulfate+amphotericin-B (GA-1000)) was added to 500 mL of a KBM-2 (KBMTM-2, CC-3103) medium was used.

[Example 4] Treatment of (Normal Human) Keratinocytes with Fine Dust and Measurement of Cytotoxicity In order to investigate the effect of treatment with fine dust on cytotoxicity, MTT assay was performed with the (normal human) keratinocytes according to the method of Mossman et al. (*J. Immunol. Methods*, 65, 55-63, 1983).

Specifically, a 24-well plate was used. The fine dust obtained in Example 2, with a diameter of 2.5 μm, was dispersed in purified water to prepare a fine dust dispersion. Then, the fine dust dispersion was applied to the cells cultured under the conditions of Example 3, with $2.5 \times 10^5$ cells per well, followed by culturing for 24 hours. Then, the cells were mixed with 5 mg/mL of MTT (3-4,5-dimethyl-thiazol-2,5-diphenyltetrazolium bromide) and further cultured at 37° C. for 3 hours. The medium was then removed and the formazan crystal formed was dissolved in 500 μL of DMSO. The lysate was aliquoted to a 96-well plate and the OD value was measured at 540 nm. The measurement result is shown in FIG. 1.

Figure 1:
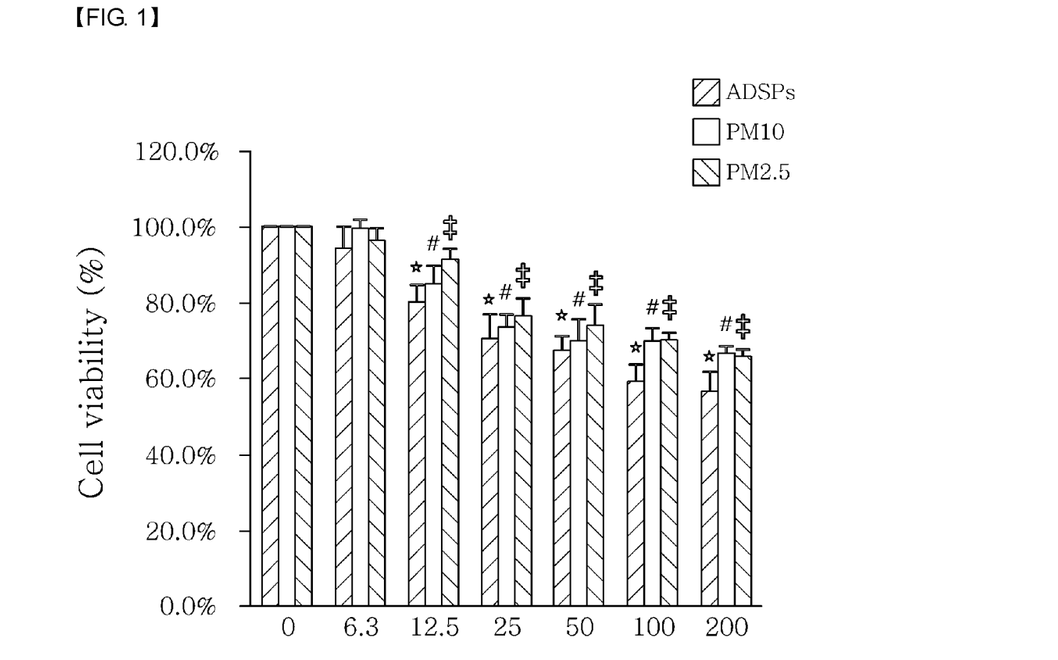
FIG. 1 shows the effect of treatment with a fine dust extract on cell viability. ADSP (Asian dust storm particle) refers to Asian dust, PM10 refers to fine dust having a particle size of 10 μm, and PM2.5 refers to fine dust having a particle size of 2.5 μm.
Figure 2A:
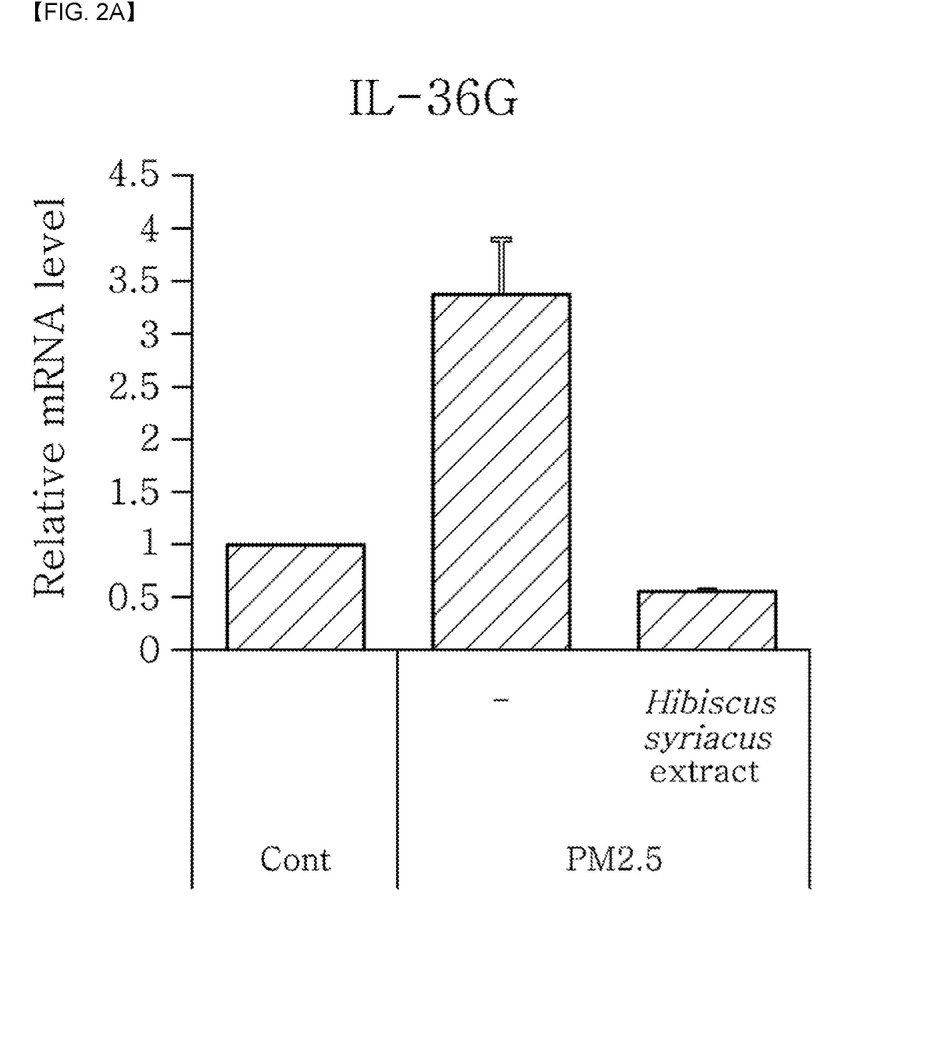
FIG. 2A shows that the mRNA expression level of the IL-36G gene is increased in skin cells irradiated by PM2.5 fine dust, and is returned to a normal level by treatment with a *Hibiscus syriacus* extract.
Figure 2B:
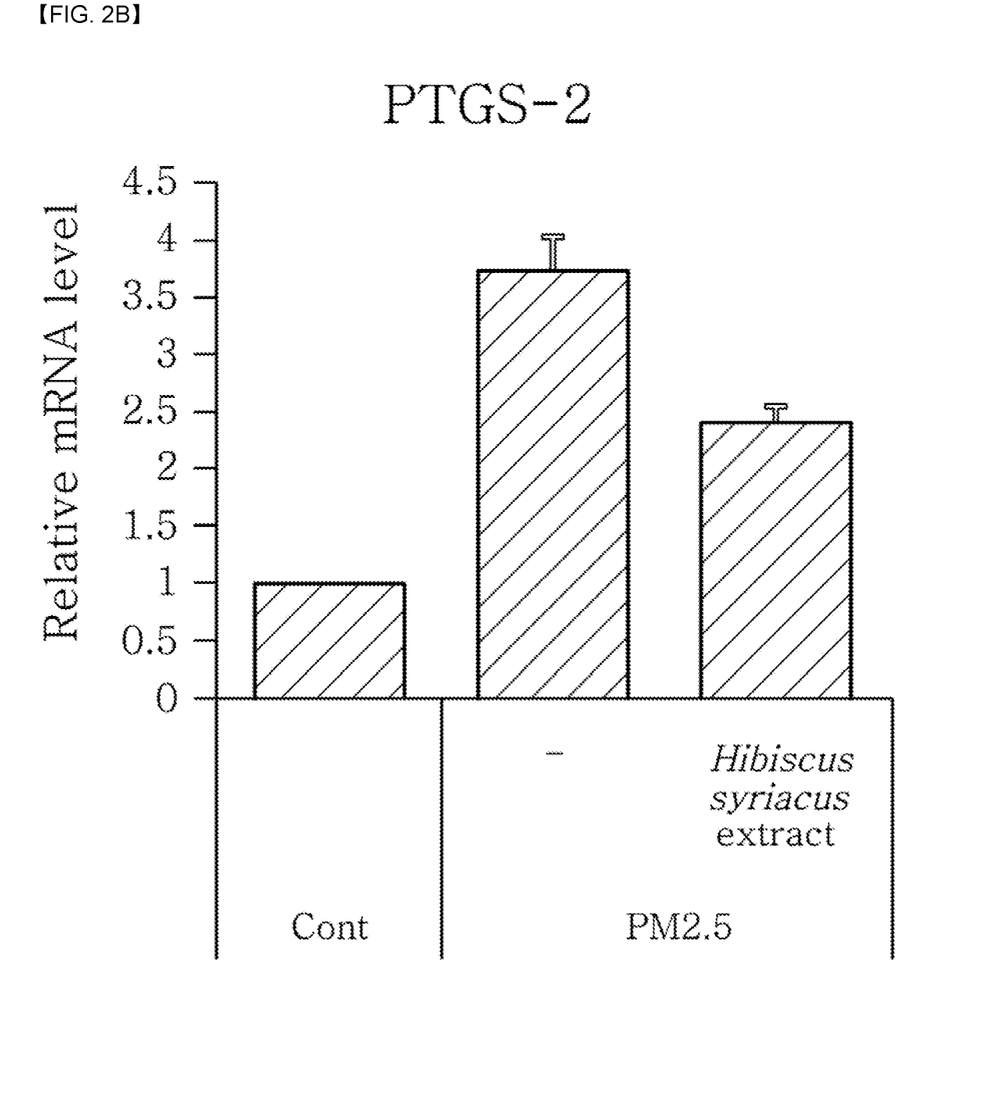
FIG. 2B shows that the mRNA expression level of the PTGS2 gene is increased in skin cells irradiated by PM2.5 fine dust, and is returned to a normal level by treatment with a *Hibiscus syriacus* extract.
Figure 2C:
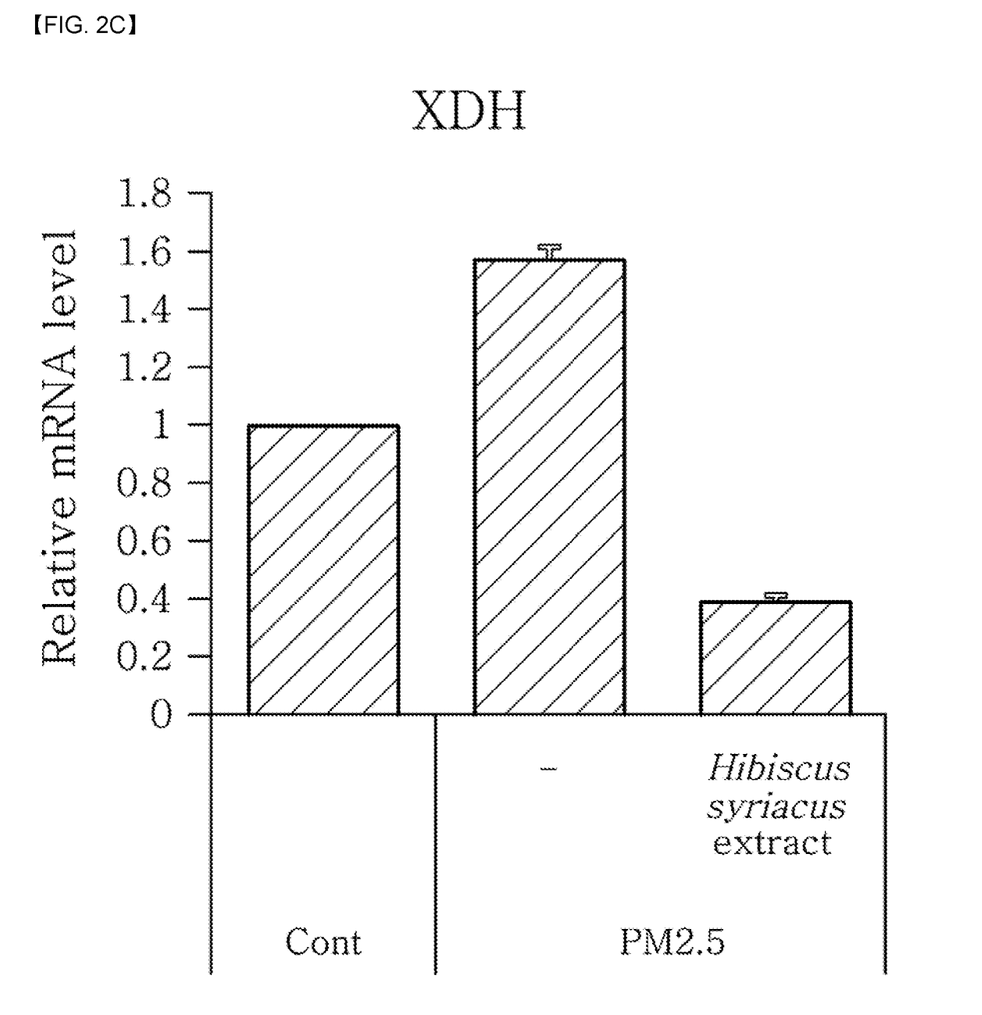
FIG. 2C shows that the mRNA expression level of the XDH gene is increased in skin cells irradiated by PM2.5 fine dust, and is returned to a normal level by treatment with a *Hibiscus syriacus* extract.
Figure 2D:
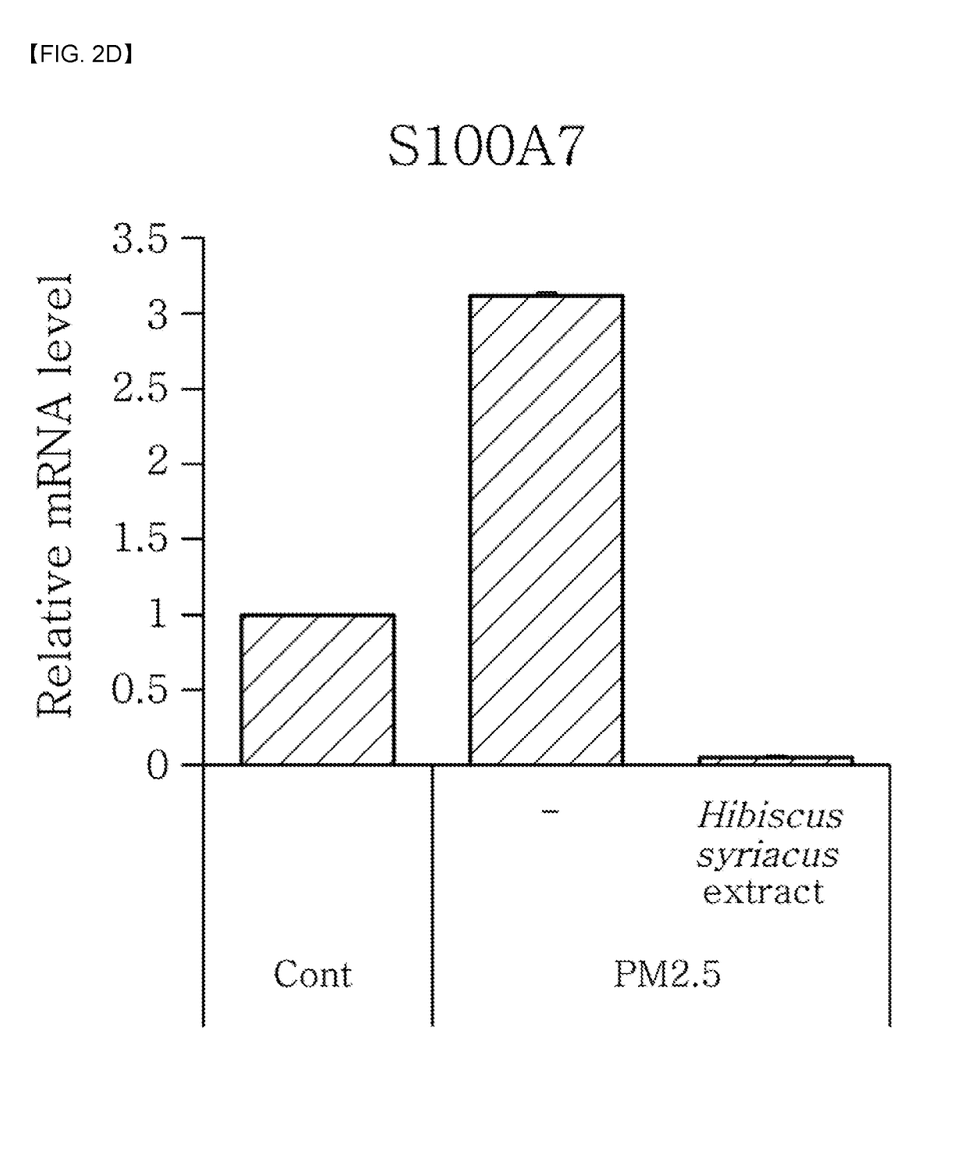
FIG. 2D shows that the mRNA expression level of the S100A7 gene is increased in skin cells irradiated by PM2.5 fine dust, and is returned to a normal level by treatment with a *Hibiscus syriacus* extract.

As shown in FIG. 1, the concentration achieving 80% cell viability (1020) for cytotoxicity caused by the dispersion obtained by dispersing fine dust with a diameter of 2.5 μm or less was 12.5 μg/mL.

[Example 5] Investigation of Change in Genes Due to Fine Dust by Next-Generation Sequencing For RNA-base sequence data processing and analysis, reference was made to the general analysis technique developed by Trapnell et al. (2012). The RNA-seq data quality was determined using FastQC (http://www.bioinformatics.babraham.ac.uk/projects/fastqc/). The base and adapter sequences with low accuracy were removed using FASTX (http://hannonlab.cshl.edu/fastx_toolkit/). Then, alignment was performed using Tophat (Trapnell et al., 2009) and a human genome (hg19), and the amount of data of each sample was determined using EVER-seq renamed to RSeQC (Wang et al., 2012). In addition, the expression level of transcripts was quantified using Cufflinks, and transcription levels were compared between the sample treated with the fine dust dispersion and a normal sample (Trapnell et al., 2010). A stringent cut-off of ≥2.0-fold change, with the FDR-adjusted p-value <0.05, was used to determine the gene that showed significant difference in expression upon treatment with the dispersion of fine dust with a diameter of 2.5 μm. The measurement result is shown in Table 3 and FIGS. 2A-2D.

TABLE 3

| Increased genes | | |
|---|---|---|
| Name | Gene symbol | Fold change |
| NM_019618 | IL36G | 7.1 |
| NM_000963 | PTGS2 | 3.7 |
| NM_000379 | XDH | 2.4 |
| NM_002963 | S100A7 | 23.8 |

[Example 6] Real-Time RT-PCR

The normal human keratinocytes cultured in Example 3 were treated with the fine dust having a diameter of 2.5 μm extracted in Example 2, with 12.5 μg per 1 mL of the cell culture medium. Then, the relative mRNA expression level was measured using the primer (Applied Biosystems TaqMan® primer) of the gene described in Table 4. The *Hibiscus syriacus* extract prepared in Example 1 was used.

TABLE 4

| Increased genes | | |
|---|---|---|
| Name | Gene symbol | TaqMan ® primer |
| NM_002963 | S100A7 | Hs00161488_m1 |

The medium was treated with 20 ppm of the *Hibiscus syriacus* extract. After 24 hours, the culture solution was removed and the cells were washed with 2 mL of phosphate-buffered saline (PBS). Then, RNA was isolated from the cells using a Trizol reagent (Invitrogen, Carlsbad, Calif., USA). The isolated RNA was further purified with the QIAGEN RNeasy kit (QIAGEN, Valencia, Calif.). Then, the quality of the RNA was determined using the Agilent 2100 BioAnalyzer (Agilent Technologies, Santa Clara, Calif., USA). cDNA was synthesized from the RNA using the Superscript Reverse Transcriptase (RT) kit (Invitrogen, Carlsbad, Calif.). The cDNA was quantitatively analyzed by real time-reverse transcription polymerase chain reaction (Q-RT-PCR) using the primers shown in Table 4. The change in the expression pattern of genes was evaluated by real-time PCR using the TaqMan gene expression assay kit (Applied Biosystems, Foster City, Calif.). The result is shown in FIGS. 2A-2D. Both of the Q-RT-PCR and the real-time PCR were performed according to the standard protocols distributed by Life Technologies. Specifically, 40 cycles of 95° C. for 20 seconds, 95° C. for 3 seconds and 60° C. for 30 seconds were performed.

FIGS. 2A-2D show that there exist genes the expression level of which is increased in the skin cells irritated by fine dust. Also, it was found that the expression level of the interleukin 36 gamma (IL-36G), prostaglandin-endoperoxide synthase 2 (PTGS2), xanthine dehydrogenase (XDH) and S100 calcium-binding protein A7 (S100A7) genes is decreased by treatment with the *Hibiscus syriacus* extract.

Therefore, it was found that the *Hibiscus syriacus* extract effectively protects skin cells from irritation by fine dust and inhibits or prevents the change in the expression level of the above-described specific genes due to the irritation, thereby returning the expression level to a normal level. In addition, it was found that the *Hibiscus syriacus* extract effectively protects skin cells from irritation by antimicrobial peptides and inhibits or prevents the change in the expression level of the above-described specific genes due to the irritation, thereby returning the expression level to a normal level.

Hereinafter, formulation examples of the compositions according to the present disclosure will be described. However, the cosmetic composition, pharmaceutical composition and health functional food composition may be formulated into various other forms. These examples are for illustrative purposes only and are not intended to limit the scope of the present disclosure.

[Formulation Example 1] Tablet 100 mg of the *Hibiscus syriacus* extract according to the present disclosure, 400 mg of lactose, 400 mg of corn starch and 2 mg of magnesium stearate were mixed and subjected to a tableting process according to a conventional method for preparing tablets to prepare a tablet.

TABLE 5

| Ingredients | Contents (mg) |
| --- | --- |
| *Hibiscus syriacus* extract | 100 |
| Lactose | 400 |
| Corn starch | 400 |
| Magnesium stearate | 2 |

[Formulation Example 2] Capsule 100 mg of the *Hibiscus syriacus* extract according the present disclosure, 400 mg of lactose, 400 mg of corn starch and 2 mg of magnesium stearate were mixed and filled in a gelatin capsule according to a conventional method for preparing capsules to prepare a capsule.

TABLE 6

| Ingredients | Contents (mg) |
| --- | --- |
| *Hibiscus syriacus* extract | 100 |
| Lactose | 400 |
| Corn starch | 400 |
| Magnesium stearate | 2 |

[Formulation Example 3] Granule 50 mg of the *Hibiscus syriacus* extract according to the present disclosure, 250 mg of anhydrous crystalline glucose and 550 mg of starch were mixed and formulated into granules using a fluidized-bed granulator. The granules were then filled in a pouch.

TABLE 7

| Ingredients | Contents (mg) |
| --- | --- |
| *Hibiscus syriacus* extract | 50 |
| Anhydrous crystalline glucose | 250 |
| Starch | 550 |

[Formulation Example 4] Soap

TABLE 8

| Ingredients | Contents (%) |
| --- | --- |
| *Hibiscus syriacus* extract | 5.00 |
| Oil and fat | q.s. |
| Sodium hydroxide | q.s. |
| Sodium chloride | q.s. |
| Fragrance | q.s. |
| Purified water | balance |

[Formulation Example 5] Lotion

TABLE 9

| Ingredients | Contents (%) |
| --- | --- |
| *Hibiscus syriacus* extract | 5.00 |
| Magnesium L-ascorbic acid-2-phosphate | 1.00 |
| Water-soluble collagen (1% aqueous solution) | 1.00 |
| Sodium citrate | 0.10 |
| Citric acid | 0.05 |
| Licorice extract | 0.20 |
| 1,3-Butylene glycol | 3.00 |
| Purified water | balance |

[Formulation Example 6] Cream

TABLE 10

| Ingredients | Contents (%) |
| --- | --- |
| *Hibiscus syriacus* extract | 3.00 |
| Polyethylene glycol monostearate | 2.00 |
| Self-emulsifying glycerin monostearate | 5.00 |
| Cetyl alcohol | 4.00 |
| Squalene | 6.00 |
| Glyceryl tri(2-ethylhexanoate) | 6.00 |
| Sphingoglycolipid | 1.00 |
| 1,3-Butylene glycol | 7.00 |
| Purified water | balance |

[Formulation Example 7] Ointment

TABLE 11

| Ingredients | Contents (%) |
|---|---|
| Hibiscus syriacus extract | 5.00 |
| Polyvinyl alcohol | 13.00 |
| Magnesium L-ascorbic acid-2-phosphate | 1.00 |
| Lauroyl hydroxyproline | 1.00 |
| Water-soluble collagen (1% aqueous solution) | 2.00 |
| 1,3-Butylene glycol | 3.00 |
| Ethanol | 5.00 |
| Purified water | balance |

[Formulation Example 8] Beauty Care Solution

TABLE 12

| Ingredients | Contents (%) |
|---|---|
| Hibiscus syriacus extract | 3.00 |
| Hydroxyethylene cellulose (2% aqueous solution) | 12.00 |
| Xanthan gum (2% aqueous solution) | 2.00 |
| 1,3-Butylene glycol | 6.00 |
| Concentrated glycerin | 4.00 |
| Sodium hyaluronate (1% aqueous solution) | 2.00 |
| Purified water | balance |

[Formulation Example 9] Health Food

TABLE 13

| Ingredients | Contents |
|---|---|
| Hibiscus syriacus extract | 2 mg |
| Vitamin A acetate | 70 μg |
| Vitamin E | 1.0 mg |
| Vitamin $B_1$ | 0.13 mg |
| Vitamin $B_2$ | 0.15 mg |
| Vitamin $B_6$ | 0.5 mg |
| Vitamin $B_{12}$ | 0.2 μg |
| Vitamin C | 10 mg |
| Biotin | 10 μg |
| Nicotinamide | 1.7 mg |
| Folic acid | 50 μg |
| Calcium pantothenate | 0.5 mg |
| Ferrous sulfate | 1.75 mg |
| Zinc oxide | 0.82 mg |
| Magnesium carbonate | 25.3 mg |
| Potassium phosphate monobasic | 15 mg |
| Calcium phosphate dibasic | 55 mg |

TABLE 13-continued

| Ingredients | Contents |
|---|---|
| Potassium citrate | 90 mg |
| Calcium carbonate | 100 mg |
| Magnesium chloride | 24.8 mg |

[Formulation Example 10] Health Drink

TABLE 14

| Ingredients | Contents |
|---|---|
| Hibiscus syriacus extract | 50 mg |
| Citric acid | 1000 mg |
| Oligosaccharide | 100 g |
| Taurine | 1 g |
| Purified water | balance |

The invention claimed is:

1. A method for treating a human with skin cells damaged by particulate matter, comprising administering a composition comprising a *Hibiscus syriacus* extract as an active ingredient to the human,
wherein the damaged skin cells express one or more genes selected from the group consisting of IL-36G (NM_019618), PTGS2 (NM_000963), XDH (NM_000379) and S100A7 (NM_002963) in an increased amount compared to prior to exposure to the particulate matter,
wherein the particulate matter has a diameter of 2.5 μm or less; and
wherein the administering of the composition decreases expression of one or more genes selected from the group consisting of IL-36G (NM_019618), PTGS2 (NM_000963), XDH (NM_000379) and S100A7 (NM_002963) in the human compared to prior to the administration.

2. The method according to claim 1, wherein the *Hibiscus syriacus* extract is comprised in an amount of 0.000001-30 wt % based on the total weight of the composition.

3. The method according to claim 1, wherein the *Hibiscus syriacus* extract is obtained by extracting *Hibiscus syriacus* with a solvent selected from the group consisting of water, a $C_1$-$C_6$ anhydrous or water-containing lower alcohol, acetone, butylene glycol, ethyl acetate, diethyl acetate, diethyl ether, benzene, chloroform, hexane, and any combination thereof.

4. The method according to claim 1, wherein the *Hibiscus syriacus* extract is an extract of bark of *Hibiscus syriacus*.

5. The method according to claim 1, wherein the composition acts on keratinocytes.

6. The method according to claim 1, wherein the *Hibiscus syriacus* extract is administered at a dosage of 10-500 mg/kg/day.

7. The method according to claim 1, wherein the composition is a cosmetic composition.

8. The method according to claim 1, wherein the composition is a health functional food composition.

* * * * *